(12) United States Patent
Ekwall

(10) Patent No.: US 6,246,909 B1
(45) Date of Patent: Jun. 12, 2001

(54) IMPLANTABLE CARDIAC STIMULATOR WHEREIN THE PACING RATE IS CONTROLLED DEPENDENT ON VARIATIONS IN THE SPONTANEOUS INTERVAL

(75) Inventor: Christer Ekwall, Spånga (SE)

(73) Assignee: Pacesetter AB, Järfälla (SE)

( * ) Notice: Subject to any disclaimer, the term of this patent is extended or adjusted under 35 U.S.C. 154(b) by 0 days.

(21) Appl. No.: 09/269,818

(22) PCT Filed: Oct. 2, 1997

(86) PCT No.: PCT/EP97/05443

§ 371 Date: Dec. 9, 1999

§ 102(e) Date: Dec. 9, 1999

(87) PCT Pub. No.: WO98/15319

PCT Pub. Date: Apr. 16, 1998

(30) Foreign Application Priority Data

Oct. 4, 1996 (SE) .................................................. 9603635

(51) Int. Cl.⁷ .................................................. A61N 1/365
(52) U.S. Cl. .................................................. 607/9
(58) Field of Search .................................. 607/9, 17, 25

(56) References Cited

U.S. PATENT DOCUMENTS 5,265,617  11/1993  Verrier et al. .
5,466,245  11/1995  Spinelli et al. .
5,713,930  * 2/1998  van der Veen et al. ................ 607/25
5,861,011  * 1/1999  Stoop ..................................... 607/25

FOREIGN PATENT DOCUMENTS

| 0 326 629 | 8/1989 | (EP) . |
| 0 358 303 | 3/1990 | (EP) . |
| 0 498 533 | 8/1992 | (EP) . |
| 0 647 454 | 4/1995 | (EP) . |
| WO 91/03274 | 3/1991 | (WO) . |
| WO 93/16756 | 9/1993 | (WO) . |

OTHER PUBLICATIONS

"Use of Hear Rate Variability to Detect Vasovagal Syncope," Research Disclosure, No. 380, Dec. 1, 1995, p. 820.

* cited by examiner

Primary Examiner—Jeffrey R. Jastrzab
(74) Attorney, Agent, or Firm—Schiff Harlin & Waite

(57) ABSTRACT

An implantable stimulating device for electrical stimulation of a heart has a stimulus generator which generates electrical stimuli and at least one lead for delivering the stimuli from the generator to the heart. A measurement unit detects spontaneous intervals between successive intrinsic heartbeats, and forms an average of at least five of these spontaneous intervals. A variation with respect to this average for later spontaneous intervals is then identified, and this variation is then used to control a pacing parameter of the stimulus generator.

7 Claims, 2 Drawing Sheets

| P | P | P | P | P |
|---|---|---|---|---|
| R | R | R | R | R |
| 117 | 115 | 112 | 102 | 105 |
| 1392 | 695 | 382 | 365 | 372 |
| 1505 | 805 | 482 | 467 | 472 |

Surface ECG
⊢— 1.0 sec. —⊣

IMPLANTABLE CARDIAC STIMULATOR WHEREIN THE PACING RATE IS CONTROLLED DEPENDENT ON VARIATIONS IN THE SPONTANEOUS INTERVAL

FIELD OF THE INVENTION

The invention relates to implantable stimulator devices capable of providing electrical stimuli to the heart. The invention particularly relates to devices in which the spontaneous rate variability is measured.

DESCRIPTION OF THE PRIOR ART

A heartbeat can be divided into two phases: the filling phase and the ejection phase. These phases are shown diagrammatically in FIGS. 1A–1E in which the two atria are indicated by A and the two ventricles by B with the heart valves indicated by C. In a first phase (FIG. 1A) the atria and ventricles are empty and blood arrives from the veins into the atria and when these are full the blood passes via the one-way heart valves into the ventricles. The atria then contract (see FIG. 1B) to pump blood from the atria into the ventricles. The state is thus reached (see FIG. 1C) in which the atria are empty whilst the ventricles are full of blood. The ventricles then contract as shown in FIG. 1D to push the blood into the arteries. This is the heart beat. After the re-expansion of the ventricles the heart has arrived at the final stage (see FIG. 1E) has now returned to the same state as the initial stage of the heartbeat cycle.

As can be seen this cycle requires the heart to act in a coordinated sequential manner. In certain heart diseases this cycle is disturbed so that for instance the ventricle does not contract immediately after filling with blood but may contract too soon or too late. In order to treat this type of disorder, use is made of the fact that electrical pulses cause muscles to contract. Pacemakers were therefore developed to provide electrical pulses at appropriate times to a diseased heart so that it would function in the same manner as a healthy heart.

The basic function of a pacemaker is to provide pacing pulses for the muscles of the heart so that a diseased heart beats in a rhythm similar to that at which a healthy heart should beat. Where possible the pacemaker only provides a pacing pulse in a situation where the natural contraction of an atrium or ventricle does not take place at the expected appropriate point in time.

Although pacemakers have been used since about 1958 and are an undoubted success they are not always able to ensure that a diseased heart always functions in the same way as a healthy heart. One reason for this is that even for healthy individuals the heart does not always beat to the same rhythm, e.g. the natural heartbeat rate varies from individual to individual. Also for a single individual the rhythm may show variations from one beat to the next.

As mentioned above there may be variations in the time between heartbeats from one beat to the next. The time length for an unpaced heartbeat cycle, i.e. the length of time for the heart to complete a cycle, is known as the spontaneous interval. The time interval between the atrial contraction (FIG. 1B) and the ventricular contraction (FIG. 1D) within a cycle is known as the AV-delay interval.

During clinical studies performed on animals, a variation in the spontaneous interval has been observed. This spontaneous interval variation (SIV) is not a result of workload, psychological or other influence. In a stable situation with no change of influence of environmental factors there may be a long spontaneous interval. This long interval is then followed by a short spontaneous interval and vice-versa. Corresponding variations in the AV-delay have been observed.

The range of variation is found to be different from one species to another, but it is always present. The interval variation in dogs has been found to be extreme compared to that of, for instance, sheep or pigs. Maximum variability is observed when the dog is awake but at rest and unstressed. On some occasions spontaneous intervals are found to vary from 412 ms (milliseconds) to 1505 ms between heartbeats under the same conditions. A corresponding variation in AV-delay is also observed (e.g. from 82 to 125 ms).

FIG. 2 shows an IEGM (intracardiac electrogram) for a dog at rest with a pacemaker operating in DDD mode at a rate of 30 per minute and an A-V delay of 250 ms. The variation in the spontaneous rate interval is clearly visible here.

It is known from literature that a low spontaneous interval variation may result from ischaemia, age and heart insufficiency. It is also known that spontaneous interval variation is the result of Vagus (Parasympathetic) nerve activity whereas heart rate increase results from Sympathetic nerve system activity.

It appears that the extreme variation in dogs is in some way connected with dogs' ability to react instantaneously, i.e. to go from rest to maximum alert with minimal delay. Also the fact that interval variation is known to be reduced in humans by disease, age and disabilities leads to the conclusion that a high variability in the spontaneous interval indicates a high reserve of available capacity. High spontaneous interval variation in humans appears to be a sign of health whereas a low spontaneous interval variation is an indicator of heart insufficiency.

The variation in the spontaneous interval causes a problem with Bradycardia stimulation. In this case the interval before a pacing pulse is given is prolonged so as to allow for a spontaneous pulse (hysteresis). This time is difficult to determine due to the spontaneous interval variation and if the hysteresis time is set too long for an unhealthy heart it can lead to a dangerously low heartbeat rate. Also, with a response rate pacemaker the maximum rate allowed may be too high for an unhealthy heart. The present invention aims to overcome these problems.

According to the abstract of U.S. Pat. No. 5,265,617 there is disclosed a device in which heart rate variability, i.e. the variability or the time between successive R-waves, together with T-wave alternans are measured and are used together for diagnosing cardiac vulnerability to ventricular fibrillation.

EP-A-647 454 states that the changes in the difference between the sensor indicated pacing rate and the actual pacing rate can be used as a measure of the time rate of change of the sensor rate. Variations in the intrinsic heart rate are not apparently measured.

According to the abstract of U.S. Pat. No. 5,466,245, in a DDD-type pacemaker the A-V delay is optimised by finding its value associated with the minimum heart rate variability index. The natural heartbeat is not used.

WO-93/16756 discloses a pacemaker in which the differences between two successive spontaneous intervals are measured. An average is taken of only the positive values of these differences.

EP-358 303 discloses taking the mean value of a number of successive spontaneous intervals. The mean value is then itself used to control a parameter.

SUMMARY OF THE INVENTION

It is an object of the present invention to provide a cardiac stimulator wherein the aforementioned problems associated with known cardiac stimulators are avoided.

The object is achieved in accordance with the principles of the present invention in an implantable stimulating device for electrical stimulation of the heart, having a stimulus generator which generates electrical pacing stimuli and at least one connection lead for delivering the stimuli from the generator to the heart, a detector for identifying spontaneous intervals between successive intrinsic heartbeats and for measuring a variation with respect to the average of at least five of these spontaneous intervals. A signal representing this variation is supplied to a control unit which controls a pacing control parameter of the stimulus generator dependent on the value of the variation.

This invention is based on the recognition that the spontaneous interval variation in the intrinsic heartbeat can be used to control parameters of a pacemaker or other device generating electrical stimuli or to monitor the heart.

These spontaneous intervals are present for almost all pacemaker patients, e.g. patients having so-called AV II-block have up to 75% spontaneous heartbeats.

Intrinsic heartbeat means the natural heartbeat without external influence which could affect it in any part of its cycle.

DESCRIPTION OF THE DRAWINGS

Referring to FIG. 3 the pacemaker is designated by 1. The electrodes 2A and 2B pace the ventricle and atrium respectively. Any suitable electrodes may be used for this purpose and may be unipolar or bipolar. Although shown in relationship to dual chamber pacing, the invention is equally applicable to single chamber pacing. The electrodes are connected by respective conduction leads 3A, 3B to a stimulation pulse generator 4.

Figure 1A:
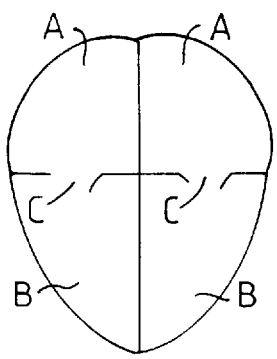
FIG. 1 shows the heart beat cycle in diagrammatic form as discussed above.
Figure 1B:
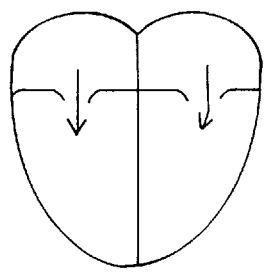
Figure 1C:
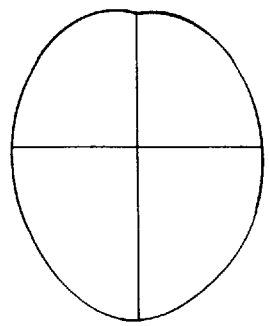
Figure 1D:
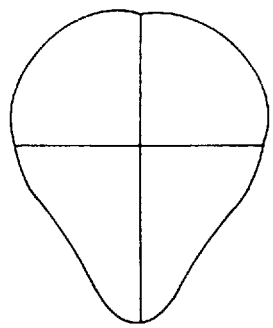
Figure 1E:
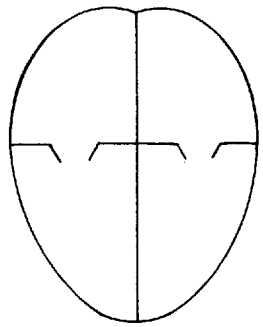
Figure 2:
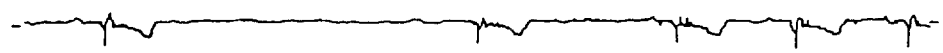
FIG. 2 shows an IEGM of a dog at rest as discussed above.

The stimulation pulse generator 4 generates and sends electrical stimuli, here in the form of pulses, to the hear through the conduction leads 3A, 3B. The pulse generator may provide pulses whose characteristics, e.g. shape, amplitude etc. may be varied. The stimulation pulse generator is controlled by a programmable controller 5. The controller 5 controls the pulse generator in response to a program contained in its memory. The program used will depend upon the heart malfunction of the patient. The program may be changed in accordance with the instruction of the patient's doctor. This change may be effected by telemetry as is known. The controller includes a clock as a timing reference for controlling the pulse generator.

Atrial and/or ventricular events are sensed by a detector 6. The time delay between two identical events on successive intrinsic heartbeat cycles corresponds to the spontaneous interval and is registered by the detector 6. In certain applications the detector registers the time delay between events on the same heartbeat cycle, e.g. the A-V delay. This time interval may be sensed in terms of a number of cycles of the pacemaker internal clock contained in the controller 5 or alternatively the detector may be provided with an independent clock.

The value of this time interval is sent to a memory 7. The memory 7 stores the values of a predetermined number of the latest recorded intervals, which is at least five and typically eight. As a new interval value is received the oldest value is deleted from the memory. The interval values are accessed by the calculator 8 for establishing a signal representative of the spontaneous interval variation (SIV). This is done in this embodiment by identifying the largest and the smallest values in the set of interval values and calculating the difference in these two values. A signal representative of this difference is stored in the calculator and then sent to the controller 5. This signal is used by the controller 5 to vary a controlling parameter of the stimulation pulse generator. This parameter will vary according to the type of pacing being used.

The functions of the controller 5, memory 7 and calculator 8 may be provided by a suitably programmed microprocessor.

In an alternative embodiment the SIV is calculated using the variance of the stored values about their means value as a statistical measure of the variability.

If the average value is changing, e.g. due to the start or cessation of exercise, this may affect the average value during the measurement and change the measurement of the SIV. This change will not however be significant compared to the value of the SIV.

The above described embodiment is particularly useful where it is desired to control the Bradycardia stimulation insertion rate. In normal pacing a stimulation insertion rate is selected. In a simple form this means that pacemaker stimulation is inhibited as long as a spontaneous beat is sensed within the selected interval. In this simple form a problem arises from competition rhythm between pacemaker and sinus (spontaneous) rhythm. In the situation where the normal heart rate is reduced from a higher level to a lower level, a certain lower rate limit is allowed before the pacemaker takes over. However if even a small statistical variation in interval length is present, a point will be reached where the spontaneous interval is alternatingly shorter and longer than the pacemaker interval.

The resulting competitive rates are undesirable for some patients and can, in the presence of retrograde conduction, even result in the so-called Pacemaker Syndrome. This is a situation where atrial contraction is simultaneous to ventricular contraction. Pressure waves then propagate backwards in the venous system (Cannon waves) as a result of atrial contraction against a closed heart valve and reduces the arterial blood flow.

In order to reduce the effects of competitive rates, hysteresis may be introduced. Hysteresis means that the interval (escape interval) before a pacing pulse is given is prolonged by a certain amount. This has the effect that in normal sinus rhythm, the rate is allowed to drop to a lower spontaneous rate than the selected or programmed pacemaker rate.

The SIV is, as already indicated above, at its maximum at rest in the healthy heart. To be effective however the hysteresis time (interval prolongation) has to be long. This creates a problem as it means that the Bradycardia stimulation insertion rate will be correspondingly low. Hysteresis with a small interval prolongation is ineffective whereas with a long prolongation it may be inappropriate. As a result hysteresis is rarely used in practice in pacemaker treatments. As a result of the invention however it is now possible to use hysteresis in practice.

In accordance with this embodiment the SIV is evaluated and used by the pacemaker to control a parameter of the pacemaker, i.e. the hysteresis time. The hysteresis time is increased in accordance with the SIV so that for a healthy heart situation—high SIV—a high hysteresis time is maintained, allowing for the high natural SIV and avoiding competition rates. In the case of a heart disorder—low SIV—the hysteresis time is reduced and low pacing rates are thus avoided.

Figure 4:
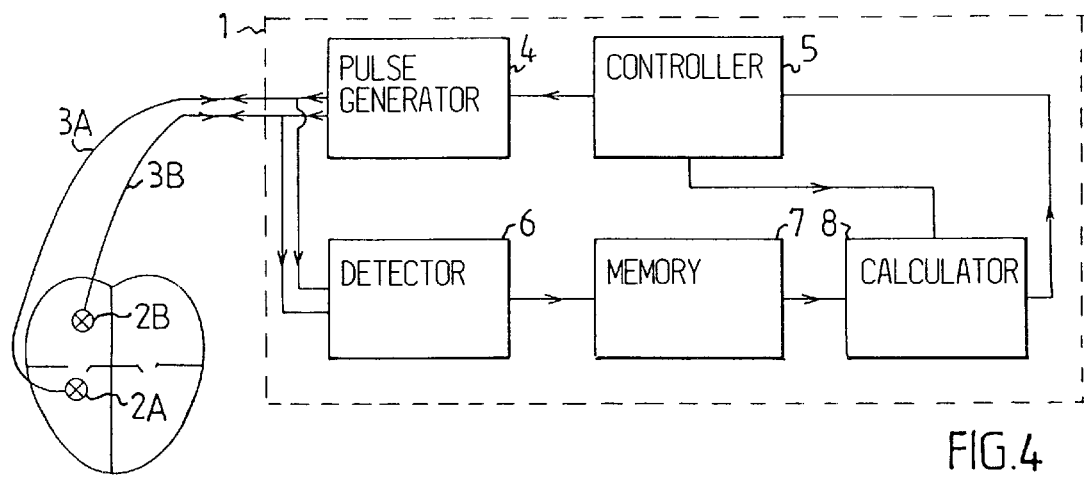
FIG. 4 shows a diagrammatic representation of a dual chamber pacemaker in accordance with a second embodiment of the invention.

FIG. 4 shows a second embodiment of the invention particularly suitable for controlling a so-called rate response pacemaker. In this type of pacemaker the pacing rate depends upon metabolic needs, i.e. workload, as measured by a sensor. However for some heart disorders a high pacing rate can result in severe inconvenience or even danger to the patient.

Figure 3:
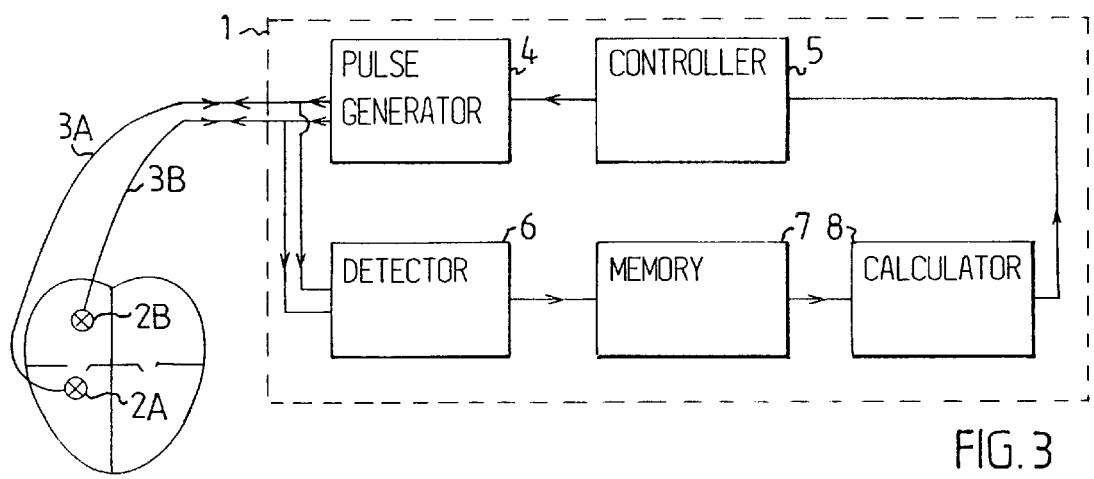
FIG. 3 shows a diagrammatic representation of a dual chamber pacemaker in accordance with a first embodiment of the invention.

The same reference numerals have been used in FIG. 4 for the same features already described with reference to FIG. 3. In this embodiment the controller 5 monitors the pacing rate. When a predetermined maximum rate is reached a signal is sent from the controller to the calculator 8. On receipt of this signal the calculator 8 ceases to access the memory to establish the new SIV and uses the last stored value. Alternatively the controller itself can store the SIV and not accept an update from calculator 8 when the predetermined maximum pacing rate is reached.

The SIV can be used to control maximum pacing rate in such a rate responsive pacemaker. When working at the maximum pacing rate in DDD mode it may be difficult to measure SIV since an interval which is spontaneous is no longer present. In this case the last value of SIV measured before a certain predetermined pacing rate has been exceeded is used to determine the maximum pacing rate allowed.

In VVI mode the spontaneous interval variation may be measured when the pacemaker is inhibited and a value thereof stored. This value may then be used when the pacemaker is not inhibited.

For AAI pacing a measure of the AV-conduction interval variation may be used to generate a measure which corresponds to the SIV. The ventricular activity is detected as the far field signal. For an AV synchronous system (e.g. VDD) the sensing of AV interval is also possible and this may be used to produce a signal representative of the spontaneous interval.

In a third embodiment depicted in FIG. 4 the invention may be used as a diagnostic monitoring device. The SIV as measured by the monitoring device may, for example, be used as an indicator of heart insufficiency between follow-ups.

Figure 5:
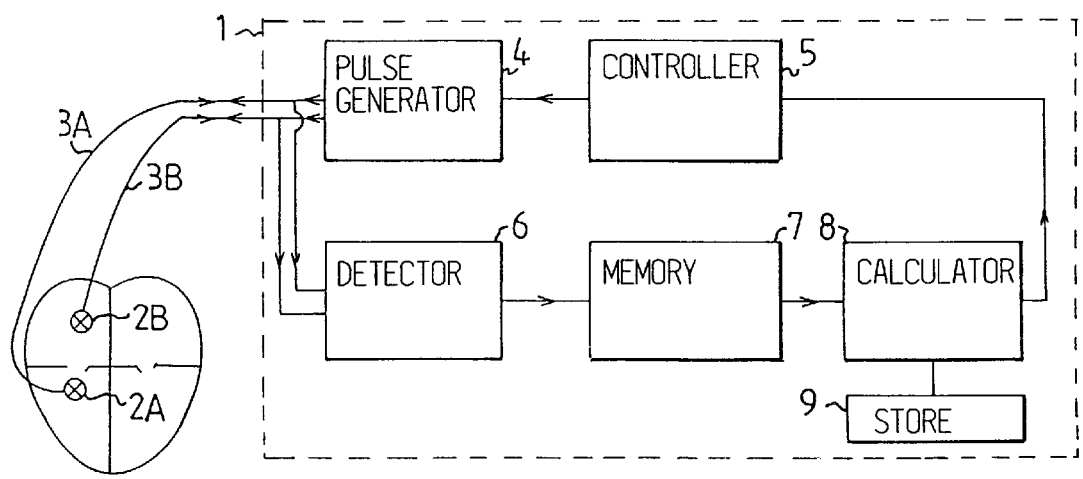
FIG. 5 shows a diagrammatic representation of a dual chamber pacemaker incorporating a third embodiment of the invention.

The monitoring device is shown in FIG. 5 in conjunction with a pacemaker, though the device may be used separately.

The same reference numerals are used in FIG. 5 for the same features as in the preceding figures. In this embodiment the calculator 8 is provided with a store 9. In the store 9, values of the SIV are stored at regular intervals. These intervals may be determined by the patient's doctor. The storing of SIV at regular intervals may also be effected with the control of the controller 5 by the calculator being set out of action.

The information may be stored such that it may be accessed by telemtry. The information may also be monitored automatically by the monitoring device. If the monitoring indicates a change in the heart condition of the patient this could be automatically indicated to the patient, for instance by an audible signal. The device is particularly, but not exclusively, useful in identifying and monitoring Ischaemia.

The extra store 9 may also be provided in the first and second embodiments of the invention.

Although the invention has been described with respect to a pacemaker and a monitoring device, it may also be used with a defibrillator.

What is claimed is:

1. An implantable stimulating device for electrical stimulation of a heart, comprising:

a stimulus generator which generates electrical pacing stimuli;

at least one lead connected to said stimulus generator and adapted to deliver said pacing stimuli from said stimulus generator to a heart;

measuring means connected to said lead for measuring respective spontaneous intervals between successive intrinsic heartbeats and for identifying a variation of an average of at least five latest spontaneous intervals of said spontaneous intervals; and a control unit supplied with said variation from said measuring means for controlling a pacing control parameter of said stimulus generator dependent on said variation.

2. A stimulating device according to claim 9 wherein said control parameter is controlled in dependence from the value of only said time interval variation.

3. A stimulating device according to claim 1 wherein said control parameter controls a hysteresis interval of said placing stimuli.

4. A stimulating device according to claim 1 wherein said control parameter controls a maximum stimulation rate.

5. A stimulating device according to claim 1 wherein said measuring means comprises a detector connected to the connection lead which detects said time interval, a memory connected to said detector for storing a predetermined number of latest detected time intervals, and a calculator for calculating and producing signals representative of the spontaneous interval variation, said calculator using said latest detected time intervals.

6. A stimulating device as claimed in claim 1 wherein said measuring means calculates said time interval variation by determining a difference between a largest value and a smallest value of a predetermined number of said time intervals.

7. A stimulating device according to claim 1 said measuring means calculates said timer interval variation by determining a variance of a predetermined number of said time intervals.

* * * * *